United States Patent [19]
Nanba et al.

[11] Patent Number: 5,169,636
[45] Date of Patent: Dec. 8, 1992

[54] LIPOSOMES

[75] Inventors: Yukihiro Nanba; Toshiyuki Sakakibara, both of Kobe; Naoto Oku, Hirakata, all of Japan

[73] Assignee: Nippon Fine Chemical Co., Ltd., Osaka, Japan

[21] Appl. No.: 445,642

[22] PCT Filed: Mar. 17, 1989

[86] PCT No.: PCT/JP89/00294
§ 371 Date: Nov. 14, 1989
§ 102(e) Date: Nov. 14, 1989

[87] PCT Pub. No.: WO88/04924
PCT Pub. Date: Jul. 14, 1988

[30] Foreign Application Priority Data

Mar. 17, 1988 [JP] Japan .................... 63-64895

[51] Int. Cl.$^5$ ............... A61K 9/127; A61K 31/715
[52] U.S. Cl. ................... 424/450; 536/4.1; 536/123; 536/1.1; 514/24; 514/25
[58] Field of Search ............ 536/1, 4.1, 5; 424/450; 514/53, 54; 428/402.2; 264/4.1, 4.3, 4.6

[56] References Cited

U.S. PATENT DOCUMENTS

| | | | |
|---|---|---|---|
| 4,189,471 | 2/1985 | Ponpipom et al. | 536/5 X |
| 4,310,505 | 1/1982 | Baldeschwieler | 424/450 |
| 4,751,219 | 6/1988 | Kempen | 424/450 |
| 4,837,028 | 6/1989 | Allen | 424/450 |
| 4,849,413 | 7/1989 | Della Valle et al. | 514/54 |
| 4,859,769 | 8/1989 | Carlsson et al. | 536/1.1 |
| 4,868,289 | 9/1986 | Magnusson et al. | 536/4.1 |
| 4,883,665 | 11/1989 | Miyazina | 424/450 |
| 4,902,512 | 2/1990 | Ishigami et al. | 424/450 |
| 4,958,016 | 9/1990 | Kerkenaar | 536/114 |

FOREIGN PATENT DOCUMENTS

WO88/04924 7/1988 World Int. Prop. O. .

OTHER PUBLICATIONS

Allen, T. M. and A. Chonn. "Large Unilamellar Liposomes with Low Uptake into the Reticuloendothelial System", FEBS Letters, vol. 223, No. 1, Oct. 1987) pp. 42–46.

Allen, Thersa M. et al. "Liposomes with Prolonged Circulation Times: Factors Affecting Uptake by Reticuloendothelial and Other Tissues", Biochimica et Biophysica Acta, vol. 981 (1989) pp. 27–35.

Gabizon, Alberto and Demetrios Papahadjopoulos. "Liposome Formulations with Prolonged Circulation Times in Blood and Enhanced Uptake by Tumors". Proc. Natl. Acad. Sci, vol. 85 Sep. 1988) pp. 6949–6953.

Primary Examiner—Thurman K. Page
Attorney, Agent, or Firm—Armstrong & Kubovcik

[57] ABSTRACT

The invention provides liposomes characterized in that the lipid membrane thereof contains a glycolipid resulting from O-glycoside or S-glycoside bonding of a lipid and at least one carbohydrate selected from the group consisting of uronic acids, uronosyl-oligosaccharides, oligosaccharides composed of glucosamine and glucuronic acid, oligosaccharides composed of galactosamine and glucuronic acid, oligosaccharides composed of glucuronic acid and xylose, oligosaccharides composed of glucuronic acid and glucose, oligosaccharides composed of glucuronic acid and galactose, oligosaccharides composed of glucuronic acid and mannose, oligosaccharides composed of galacturonic acid and rhamnose, ketoaldonic acids, 2-acetamido-2-deoxyuronic acids, 2-acetamido-2-deoxyuronic acid-containing oligosaccharides, 6-O-carboxyethyl-$\beta$-D-glucose, 6-O-carboxymethyl-$\beta$-D-glucose, 6'-O-carboxymethyl-$\beta$-D-maltose and 6'-O-carboxyethyl-$\beta$-D-maltose.

7 Claims, 1 Drawing Sheet

LIPOSOMES

TECHNICAL FIELD

This invention relates to liposomes and, more particularly, to liposomes which can remain in the blood at a high concentration level for a prolonged period of time while avoiding uptake thereof by reticuloendothelial system (RES) tissues.

BACKGROUND ART

Liposomes are closed vesicles composed of one or more lipid membranes mainly consisting of phospholipids and are used as models of biological membranes in physicochemical studies thereof. Furthermore, they can entrap various substances in the inside aqueous phase or in the membranes and therefore they have become a target of intensive investigations of their use as one of drug delivery systems containing various drugs entrapped therein. As regard the use thereof as such delivery system, there may be mentioned, among others, the report of B. E. Ryman et al. [Ann. N. Y. Acad. Sci., 308, 281 (1978)], the report of G. Gregoridias ("Liposome Technology", CRC Press Inc.) and the report of J. N. Weinstein [Science, 204, 188 (1979)]. In particular, they are effective in reducing the toxicity of highly toxic drugs, stabilizing drugs otherwise unstable in vivo and achieving sustained release of drugs in vivo. It is further known that they can be used as means of directing drugs to particular cells selectively by utilizing their property of fusing with cells or being taken up by cells. In a typical example of their application, liposomes are combined with, for example, enzymes (superoxide dismutase etc.), drugs (in particular antitumor agents, adriamycin), chelating agents, hormones (steroid compounds), radionuclides, interferons, interleukins, antigens and antibodies. It is also known that the duration of the efficacy of a drug showing a brief blood half-life, such as insulin, can be prolonged by entrapping it in liposomes. A therapy (missile therapy) has been developed as well which uses anticancer agent-containing liposomes combined with tumor surface-specific antigens bound thereto for selectively attacking cancer cells.

However, in their use in vivo, liposomes administered to the living body are captured by reticuloendothelial system tissues in a short time. This capture is a result of liposomes, which are macromolecules, being recognized as a foreign matter. Such characteristic is a great drawback when it is intended to direct liposomes to tissues other than RES tissues or to increase the duration of the efficacy of a drug in the blood circulation.

For removing such drawback, liposomes containing sialic acids in their lipid bilayer have been proposed (U.S. Pat. No.4,501,728). However, these liposomes cannot avoid capture by the RES to a sufficient extent, either, so that they cannot produce a satisfactory drug efficacy prolonging effect.

DISCLOSURE OF THE INVENTION

It is an object of the invention to provide liposomes which are hardly captured by the RES and can remain in the blood at a high concentration level over a prolonged period of time.

Other objects and features of the invention will become apparent from the description which follows.

Thus the invention provides liposomes characterized in that the liposome lipid membrane contains a glycolipid resulting from O-glycoside or S-glycoside bonding of a lipid and at least one carbohydrate selected from the group consisting of uronic acids, uronosyl-oligosaccharides, oligosaccharides composed of glucosamine and glucuronic acid, oligosaccharides composed of galactosamine and glucuronic acid, oligosaccharides composed of glucuronic acid and xylose, oligosaccharides composed of glucuronic acid and glucose, oligosaccharides composed of glucuronic acid and galactose, oligosaccharides composed of glucuronic acid and mannose, oligosaccharides composed of galacturonic acid and rhamnose, ketoaldonic acids, 2-acetamido-2-deoxyuronic acids, 2-acetamido-2-deoxyuronic acid-containing oligosaccharides, 6-O-carboxyethyl-$\beta$-D-glucose, 6-O-carboxymethyl-$\beta$-D-glucose, 6'-O-carboxymethyl-$\beta$-D-maltose and 6'-O-carboxyethyl-$\beta$-D-maltose.

As a result of their investigations, the present inventors found that liposomes containing specific glycolipids other than sialic acids in their lipid membrane are hardly captured by the RES and can remain in the blood at a high concentration level for a long period of time and that said liposomes, which have such significant effects, make it possible to maintain unexpectedly high drug concentrations in the blood for a long period and therefore very useful in the pharmaceutical field, for example in making up anticancer preparations, enzyme preparations, and protein or peptide preparations. On the basis of these findings, they have now completed the present invention.

The glycolipid to be incorporated into the lipid bilayer of liposomes in accordance with the invention is one resulting from O-glycoside or S-glycoside bonding of a carbohydrate and a lipid, each mentioned hereinbelow.

Usable as the carbohydrate is at least one carbohydrate selected from the group consisting of uronic acids, uronosyl-oligosaccharides, oligosaccharides composed of glucosamine and glucuronic acid, oligosaccharides composed of galactosamine and glucuronic acid, oligosaccharides composed of glucuronic acid and xylose, oligosaccharides composed of glucuronic acid and glucose, oligosaccharides composed of glucuronic acid and galactose, oligosaccharides composed of glucuronic acid and mannose, oligosaccharides composed of galacturonic acid and rhamnose, ketoaldonic acids, 2-acetamido-2-deoxyuronic acids, 2-acetamido-2-deoxyuronic acid-containing oligosaccharides, 6-O-carboxyethyl-$\beta$-D-glucose, 6-O-carboxymethyl-$\beta$-D-glucose, 6'-O-carboxymethyl-$\beta$-D-maltose and 6'-O-carboxyethyl-$\beta$-D-maltose. These carbohydrates are mono- or disaccharides having at least one carboxyl group on the saccharide chain thereof.

As the uronic acids, there may be mentioned, for example, L-iduronic acid, D-galacturonic acid, D-glucuronic acid, L-glucuronic acid, D-mannuronic acid, etc.

As the uronosyl-oligosaccharides, there may be mentioned, for example, 2-$\beta$-glucuronosylglucuronic acid, $\alpha$-1,4'-galacturonosylgalacturonic acid, 4-$\beta$-mannuronosylmannuronic acid, 2-$\beta$-glucuronosylglucuronic acid, etc.

As the oligosaccharides composed of glucosamine and glucuronic acid, there may be mentioned, for example, hyalobiouronic acid, heparosin, etc.

As the oligosaccharides composed of galactosamine and glucuronic acid, there may be mentioned, for example, chondrosin etc.

As the oligosaccharides composed of glucuronic acid and xylose, there may be mentioned, for example 4-β-glucuronoxylose, 3-α-glucuronoxylose, 2-α-glucuronoxylose, 2-α-4-O-methylglucuronoxylose, 3-α-4-O-methylglucuronoxylose, etc.

As the oligosaccharides composed of glucuronic acid and glucose, there may be mentioned, for example, cellobiouronic acid etc.

As the oligosaccharides composed of glucuronic acid and galactose, there may be mentioned, for example, 6-β-glucuronogalactose etc.

As the oligosaccharides composed of glucuronic acid and mannose, there may be mentioned, for example, 2-β-glucuronomannose etc.

As the oligosaccharides composed of glacturonic acid and rhamnose, there may be mentioned, for example, 2-α-galacturono-L-rhamnose etc.

As the ketoaldonic acids, there may be mentioned, for example, D-arabinose-hexuronic acid etc.

6-O-Carboxyethyl-β-D-glucose can be produced, for example, by reacting 1,2,3,4-tetra-O-benzyl-β-D-glucose, which is obtainable by benzylation of glucose, with succinic anhydride and then subjecting the reaction product to debenzylation.

6-O-Carboxymethyl-β-D-glucose can be produced, for example, by reacting 1,2,3,4-tetrabenzyl-β-D-glucose with methyl bromoacetate in the presence of sodium hydride and subjecting the reaction product to hydrolysis of the methyl ester moiety and to debenzylation by catalytic reduction.

6'-O-Carboxymethyl-β-D-maltose can be produced, for example, by reacting 1,2,3,6-2',3',4'-heptabenzylmaltose, which is obtainable by benzylation of maltose, with ethyl bromoacetate in the presence of sodium hydride and subjecting the reaction product to hydrolysis of the ethyl ester moiety and to debenzylation by catalytic reduction.

Among the above-mentioned carbohydrates, uronic acids, uronosyl-oligosaccharides, oligosaccharides composed of glucosamine and glucuronic acid, oligosaccharides composed of galactosamine and glucuronic acid, oligosaccharides composed of glucuronic acid and galactose, oligosaccharides composed of glucuronic acid and mannose, and the like are preferred. Uronic acids, uronosyl-oligosaccharides, oligosaccharides composed of glucosamine and glucuronic acid, oligosaccharides composed of galactosamine and glucuronic acid, and the like are particularly preferred.

The lipid to form a glycolipid with the carbohydrate mentioned above through O- or S-glycoside bonding may be any known one. The use of at least one member selected from among diacylglycerides, dialkylglycerides, sphingosines, ceramides, hydrocarbons and cholesterol is preferred among others, however.

As the diacylglycerides, there may be mentioned, for example, 1,2-diacylglycerides whose acyl moieties are saturated or unsaturated acyl groups containing about 10 to 40 carbon atoms, such as 1,2-dipalmitoylglyceride, 1,2-distearoylglyceride and 1,2-dioleoylglyceride.

As the dialkylglycerides, there may be mentioned, for example, 1,2-O-dialkylglycerides whose alkyl moieties are straight or branched alkyl groups containing about 10 to 40 carbon atoms, such as 1,2-O-dihexadecylglyceride and 1,2-O-dioctadecylglyceride.

As the hydrocarbons, there may be mentioned, for example, saturated or unsaturated, straight or branched aliphatic hydrocarbons containing about 10 to 60 carbon atoms, preferably about 14 to 40.

The above-mentioned lipid may be a single substance or a mixture of two or more species.

The glycolipid to be used in accordance with the invention can be produced by subjecting the above-mentioned carbohydrate and lipid to a known glycoside formation process, for example the Koenigs-Knorr synthesis.

In the practice of the invention, a known lipid other than a glycolipid, for example a phospholipid or cholesterol, is also used as a liposome membrane constituent element in combination with the above-mentioned glycolipid. The phospholipid may be any known one and, as typical examples thereof, there may be mentioned, for example, phospholipids such as soybean lecithin, yolk lecithin, dipalmitoylphosphatidylcholine, distearoylphosphatidylchloline, dioleoylphosphatidylcholine, phosphatidylethanolamine, phosphatidylglycerol, sphingomyelin, phosphatidylinositol, etc., and hydrogenation products from natural phospholipids, such as hydrogenated lecithin. For further preventing fusion among liposomes or leakage of entrapped substance, cholesterol as well as charge-bearing phospholipids, such as phosphatidic acid, phosphatidylserine, phosphatidylglycerol and cardiolipin, may be used in combination with other phospholipids. The above-mentioned phospholipids may be used either singly or in combination in the form of a mixture of two or more.

In the practice of the invention, straight or branched, saturated or unsaturated fatty acids containing about 10 to 40 carbon atoms or diglycerides or triglycerides or cholesterol esters of such fatty acids may also be used as liposome membrane constituents in addition to the above-mentioned lipids, as necessary.

The liposomes according to the invention may have any known liposome form. As typical examples of such form, there may be mentioned, for example, the multilamellar vesicle (MLV) form, the small unilamellar vesicle (SUV) form, the large unilamellar vesicle (LUV) form, etc.

The liposomes according to the invention can be produced by a known method. As example of such method is mentioned below.

First, a lipid, a glycolipid according to the invention and, if necessary, cholesterol are dissolved in an appropriate solvent. Then, the solution obtained is placed in a rotary evaporator, for instance, and the solvent is distilled off, whereby a lipid film is formed on the inside wall surface of the evaporator. An aqueous solution or buffer solution of a substance to be included is added to the evaporator and the evaporator is shaken vigorously, whereby a dispersion of the liposomes according to the invention can be obtained. If necessary, freezing and thawing and/or ultrasonic treatment may be conducted after shaking. Sizing with respect to the liposome diameter may also be performed using a polycarbonate film.

The amount of phospholipid to be used is not particularly critical but may be selected properly depending on the substance to be liposomally included and on other factors. The amount of glycolipid to be used is not particularly critical, either. When the ease of liposome formation, among others, is taken into consideration, however, it is advisable to use the glycolipid in an amount such that it is contained in the lipid membrane at a level of about 1 to 50 mole percent, preferably about 5 to 30 mole percent. The substance to be included or entrapped may be selected properly depending on the intended use of the desired liposomes from among those substances that are known as substances capable of being entrapped in liposomes, for example drugs and markers. The level of addition of the substance to be included is not particularly critical but may be selected properly. Any solvent capable of dissolving the lipids to be used can be used as an appropriate solvent. As examples, there may be mentioned halogenated hydrocarbons such as chloroform, methyl chloroform, methylene chloride, etc., hydrocarbons, such as hexane, heptane, etc., aromatic hydrocarbons such as benzene, toluene, xylene, etc., ethers such as diethyl ether, diisopropyl ether, ethylene glycol dimethyl ether, tetrahydrofuran, etc., and so forth. The temperature conditions in the step of lipid film formation by solvent removal by distillation are not particularly critical but can be selected properly within the broad range of about 0° to 100° C. For preventing lipid oxidation, however, the temperature should be selected within the range of about 25° C. to 60° C., more preferably within the range of about 30° C. to 40° C. The pH and salt concentration in preparing liposomes are not particularly critical provided that they will not cause denaturation of the lipids and the liposomes. Generally, however, the pH should advisably be adjusted to about 7 and the osmolarity to about 0.3.

The product liposomes can be separated from that portion of the drug, marker or the like which remain untrapped by liposomes by purifying the liposome suspension obtained in the above manner by known purification means, such as gel filtration, centrifugation, etc. Addition of an aqueous buffer solution (Tris, phosphoric acid, HEPES, MOPS, etc.) so prepared that it is isotonic to the solution included in liposomes to the liposomes separated in the above manner gives a suspension of the liposomes according to the invention which contain the above-specified glycolipid. That the above procedure can give the liposomes according to the invention is apparent from the findings obtained in the experimental example mentioned later herein that liposomes obtained by the same procedures mentioned above can remain in the blood circulation at a high concentration level for a long period and can hardly be captured by the RES.

The diameter of the liposomes according to the invention is not particularly critical. Generally, however, the liposomes should advisably have a diameter of about 0.03 to 0.8 $\mu$m, preferably about 0.05 to 0.5 $\mu$m.

EXAMPLES

The following examples illustrate the invention in further detail.

REFERENCE EXAMPLE 1 (SYNTHESIS OF GLYCOLIPID)

Methyl D-glucopyranosyluronate was prepared by methylating glucuronolactone (Nakarai Tesque, formerly Nakarai Chemicals) in methanol in the presence of a catalytic amount of sodium methylate. This was acetylated with acetic anhydride in pyridine to give methyl (2,3,4-tri-O-acetyl-$\beta$-D-glucopyranosyl uronate, which was further brominated in acetic acid saturated with hydrogen bromide. Thus was synthesized methyl (2,3,4-tri-O-acetyl-$\alpha$-D-glucopyranosyl bromide)uronate. This was reacted with palmityl alcohol in the presence of silver carbonate at 25° C. Recrystallization of the product from ethanol gave methyl (hexadecyl 2,3,4-tri-O-acetyl-$\beta$-D-glucopyranosyl)uronate in 50% yield (from glucuronolactone). Furthermore, this was deacetylated with a catalytic amount of sodium methylate in methanol and the reaction mixture was evaporated to dryness. The residue obtained was suspended in 50% aqueous methanol, potassium hydroxide was added and hydrolysis of the ester moiety was carried out. The hydrolyzate was adjusted to pH 3 with diluted hydrochloric acid and extracted with chloroform/methanol (2/1) to give hexadecyl $\beta$-D-glucopyranosyluronate (hereinafter referred to as "glycolipid A") as light yellow crystals in 30% yield (from glucuronolactone).

EXAMPLE 1

Liposomes were produced as described below using $^{14}$C-labeled tripalmitin as one of liposome membrane constituents and $^3$H-inulin as the substance entrapped in liposomes, for submitting the liposomes obtained in this example to the reticuloendothelial system avoidance test and blood level test mentioned later herein.

A solution of 80 micromoles of dipalmitoylphosphatidylcholine (DPPC), 80 micromoles of cholesterol and 40 micromoles of glycolipid A in 20 ml of chloroform-methanol (2:1, v/v) was added to an eggplant type flask, followed by further addition of 30 $\mu$Ci of $^{14}$C-tripalmitin. The solvent was then distilled off on a rotary evaporator. Onto the film formed in the flask were added 0.79 ml of sterilized distilled water and 200 $\mu$Ci (0.2 ml) of $^3$H-inulin. The mixture in the flask was stirred by means of a vortex mixer until the film had peeled off. The emulsion obtained was freezed with liquefied nitrogen and then thawed on warm water (40° C.). After two repetitions of this cycle, 0.11 ml of sterilized 3M glucose was added to the emulsion, followed by two repetitions of the freezing and thawing cycle. The emulsion obtained was passed through a 0.1-$\mu$m membrane filter twice. The so-treated emulsion was centrifuged at 3,000 rpm for 5 minutes. The upper layer was separated, diluted to 3.2 ml with sterilized 0.15M NaCl and centrifuged at 50,000 rpm for 30 minutes. To the sediment was added sterilized 0.15M NaCl to give 2.5 ml of a suspension. After one more repetition of the same procedure, there was obtained 3.2 ml of a suspension of glycolipid-containing liposomes (0.17 $\mu$m in diameter) according to the invention.

COMPARATIVE EXAMPLE 1

The procedure of Example 1 was followed in the same manner except that 40 micromoles of dipalmitoylphosphatidylglycerol (DPPG) was used in lieu of glycolipid A. There was obtained 3.2 ml of a glycolipid-free liposome suspension.

EXPERIMENTAL EXAMPLE 1

(Measurement of rates of distribution of $^{14}$C and $^3$H in serum and tissue)

The following test was performed using the liposome suspensions obtained in Example 1 and Comparative Example 1.

Each liposome suspension was injected into rats via the jugular vein at a dose of 0.5 ml per animal. Blood sampling was performed 5, 15, 30 and 60 minutes and 1, 2, 4, 6 and 20 hours after injection from the femoral vein. Each blood sample collected was centrifuged at 2,000 rpm for 5 minutes, a 30-$\mu$l portion of the serum fraction was taken, 1 ml of a tissue dissolving agent (Soluen, Merk) was added and, after 2 hours of treatment at 40° C., aqueous hydrogen peroxide and isopropyl alcohol were added. The resultant mixture was used as an assay sample. At 20 hours after injection, the liver was excised from each rat and a portion thereof was treated in the same manner as in the case of serum to give an assay sample.

The samples prepared as described above were assayed for $^{14}C$ and $^{3}H$ using a liquid scintillation counter. Based on the values obtained, the blood concentration (the concentration upon injection being taken as 100) at each specified time and the percent distribution in liver after 22 hours were calculated. The results thus obtained are shown below in Table 1 and Table 2. Each value is a mean of the values for 5 rats.

TABLE 1

Changes in liposome concentration in blood as function of time

| Time | Example 1 $^{14}C$ | Example 1 $^{3}H$ | Comparative Example 1 $^{14}C$ | Comparative Example 1 $^{3}H$ |
|---|---|---|---|---|
| 5 min | 98.0 | 99.8 | 97.0 | 99.1 |
| 15 min | 97.0 | 99.4 | 98.0 | 99.0 |
| 30 min | 92.0 | 97.6 | 94.9 | 95.2 |
| 1 hr | 95.0 | 96.1 | 89.0 | 89.0 |
| 2 hr | 88.0 | 88.5 | 80.0 | 81.0 |
| 4 hr | 76.0 | 77.0 | 73.0 | 65.0 |
| 6 hr | 66.2 | 67.3 | 60.0 | 62.0 |
| 8 hr | 58.5 | 56.2 | 42.0 | 40.1 |
| 22 hr | 27.3 | 28.2 | 9.0 | 9.4 |

The data shown in Table 1 indicate that the liposomes (according to the invention) of Example 1 were present in the blood at higher concentration levels over a longer period of time as compared with the liposomes (for comparison) of Comparative Example 1. Upon graphic representation of the data, this becomes more apparent. Thus, as shown in FIG. 1, which shows the changes in $^{3}H$-inulin level in blood as a function of time, the blood level of the liposomes according to the invention after 8 hours was 1.4 times and that after 20 hours was 3 times the corresponding level of the liposomes for comparison.

TABLE 2

| | Distribution of liposomes in liver | |
|---|---|---|
| | Example 1 | Comparative Example 1 |
| $^{14}C$ | 12.3 | 17.1 |
| $^{3}H$ | 19.3 | 32.2 |

As seen in Table 2, the distribution of $^{14}C$ and that of $^{3}H$ in the liver were considerably lower with the liposomes according to the invention than with the liposomes for comparison, indicating that the liposomes according to the invention are very hardly taken up by reticuloendothelial system tissue (liver) as compared with the liposomes for comparison.

In view of the above results, it can be concluded that the liposomes according to the invention can avoid uptake by reticuloendothelial system tissues and maintain a high blood level for a long period of time.

Figure 1:
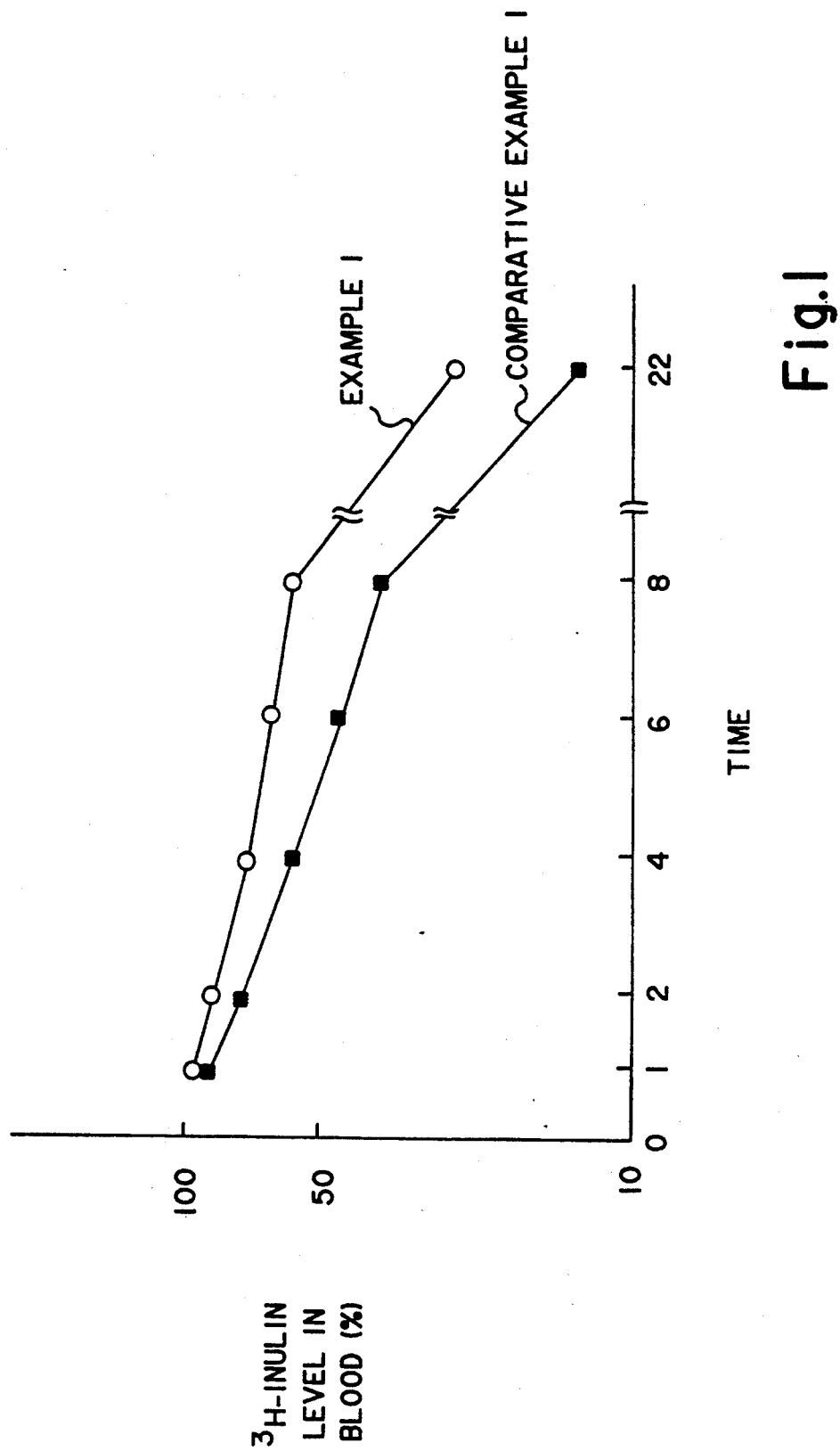
FIG. 1 shows changes in $^{3}H$-inulin concentration in blood each as a function of time.

We claim:

1. A liposome comprising a lipid membrane which contains a glycolipid resulting from O-glycoside or S-glycoside bonding of a lipid and at least one carbohydrate selected from the group consisting of uronic acids, uronosyl-oligosaccharides, oligosaccharides composed of glucosamine and glucuronic acid, oligosaccharides composed of galactosamine and glucuronic acid, oligosaccharides composed of glucuronic acid and xylose, oligosaccharides composed of glucuronic acid and glucose, oligosaccharides composed of glucuronic acid and galactose, oligosaccharides composed of glucuronic acid and mannose, oligosaccharides composed of galacturonic acid and rhamnose, ketoaldonic acids, 2-acetamido-2-deoxyuronic acids, 2-acetamido-2-deoxyuronic acid-containing oligosaccharides, 6-O-carboxyethyl-$\beta$-D-glucose, 6-O-carboxymethyl-$\beta$-D-glucose, 6'-O-carboxymethyl-$\beta$-D-maltose and 6'-O-carboxyethyl-$\beta$-D-maltose.

2. The liposome of claim 1, wherein the carbohydrate is at least one member selected from the group consisting of uronic acids, uronosyl-oligosaccharides, oligosaccharides composed of glucosamine and glucuronic acid, oligosaccharides composed of galactosamine and glucuronic acid, oligosaccharides composed of glucuronic acid and galactose and oligosaccharides composed of glucuronic acid and mannose.

3. The liposome of claim 1, wherein the carbohydrate is at least one member selected from the group consisting of uronic acids, uronosyl-oligosaccharides, oligosaccharides composed of glucosamine and glucuronic acid, and oligosaccharides composed of galactosamine and glucuronic acid.

4. The liposome of claim 1, wherein the carbohydrate is at least one member selected from the group consisting of a uronic acids and a uronosyl-oligosaccharide.

5. The liposome of claim 1, wherein the lipid forming an O-glycoside or S-glycoside bond with the carbohydrate is at least one member selected from the group consisting of diacylglycerides, dialkylglycerides, sphingosines, ceramides, cholesterol and saturated or unsaturated straight or branched aliphatic hydrocarbons containing about 10 to about 60 carbon atoms.

6. The liposome of claim 1, wherein the lipid membrane contains the glycolipid in an amount of 1 to 50 mole percent.

7. The liposome of claim 5, wherein the lipid membrane contains the glycolipid in an amount of 5 to 30 mole percent.

* * * * *